United States Patent [19]

Mizuno

[11] Patent Number: 5,226,903
[45] Date of Patent: Jul. 13, 1993

[54] APPARATUS FOR OPHTHALMIC OPERATION USING PHOTOCOAGULATION BY A LASER BEAM

[75] Inventor: Katsuyasu Mizuno, Aichi, Japan

[73] Assignee: Nidek Co., Ltd., Aichi, Japan

[21] Appl. No.: 827,621

[22] Filed: Jan. 29, 1992

[30] Foreign Application Priority Data

Jan. 30, 1991 [JP] Japan .................................. 3-029416

[51] Int. Cl.[5] ............................................. A61B 17/36
[52] U.S. Cl. .......................................... 606/17; 606/4; 606/10; 128/395
[58] Field of Search ........................ 606/5, 17, 4, 6, 10; 128/395

[56] References Cited

U.S. PATENT DOCUMENTS

| | | |
|---|---|---|
| 4,409,979 | 10/1983 | Roussel et al. |
| 4,669,837 | 6/1987 | Schirmer et al. |
| 4,776,335 | 10/1988 | Nakanishi et al. ............ 128/395 |
| 4,917,486 | 4/1990 | Raven et al. |

FOREIGN PATENT DOCUMENTS

| | | |
|---|---|---|
| 0230094 | 7/1987 | European Pat. Off. |
| 91/01703 | 2/1991 | PCT Int'l Appl. |

Primary Examiner—Stephen C. Pellegrino
Assistant Examiner—Sonya Harris
Attorney, Agent, or Firm—Finnegan, Henderson, Farabow, Garrett & Dunner

[57] ABSTRACT

An apparatus for performing an ophthalmic operation on an eye by photocoagulation using a laser beam while allowing continuous observation of the eye to be treated, includes a light source for producing the laser beam, an observing system having a first inherent optical path including a slit-lamp microscope, a laser optical system having a second inherent optical path, means for transmitting the laser beam from the light source to the laser optical system, means for introducing the laser beam from the second optical path of the laser optical system to the first optical path of the observing system, a contact lens having predetermined characteristics positioned in front of and contacting the eye to be treated, first optical means provided in the first inherent optical path of the observing system for adjusting an objective plane observable from the slit-lamp microscope, means for shifting the objective plane to a desired position along the optical path while observing the objective plane, and second optical means provided in the second inherent optical path of the laser optical system for adjusting a focal point, the laser beam being controlled while adjusting the focal point along the second optical path of the laser optical system, wherein the first optical means controls the movement of the objective plane observed from the observing system according to the predetermined characteristics of the contact lens and the second optical means adjusts the focal point to direct the laser beam on the objective plane.

20 Claims, 9 Drawing Sheets

APPARATUS FOR OPHTHALMIC OPERATION USING PHOTOCOAGULATION BY A LASER BEAM

BACKGROUND OF THE INVENTION

1. Field of the Invention

The present invention relates to an apparatus for performing an ophthalmic operation by photocoagulation using a laser beam, and, more particularly, to an apparatus for performing an ophthalmic operation in which an affected part in the fundus of a patient's eye is irradiated by a spot laser beam emitted from a laser optical system while an oculist observes the fundus of the patient's eye covered with one of two types of contact lenses using an observing system including a slit-lamp microscope.

2. Description of Related Art

A conventional apparatus for an ophthalmic operation using a laser beam is shown in FIG. 8 in which the ophthalmic operation is conducted by introducing the laser beam for ophthalmic treatment into an observing system including a slit-lamp microscope.

In FIG. 8, a laser diode capable of emitting a high power laser beam with wavelength of 800 nm, that is used for ophthalmic treatment, and a He-Ne laser source for aiming a spot laser beam with wavelength of 633 nm on the fundus of a patient's eye, are provided in the laser beam light source box 1. The laser beams emitted from both the laser diode and the He-Ne laser source are transmitted to a housing 3 of a laser optical system through an optical fiber 2.

The housing 3 is attached through a hole 5 of the slit-lamp body (indicated by a dashed line) and used for mounting a diopter adjustment bar. The laser beam from an edge plane 18 of the optical fiber 2 is transmitted to a dichroic mirror 11 through lenses 6, 9 and 10. The dichroic mirror 11 has the characteristics of (1) reflecting the light beam with wavelength of 800 nm and (2) reflecting half of visible light and transmitting the remaining half thereof. As a result, the optical axis of the laser optical system becomes coaxial with the optical axis of the observing system that includes a slit-lamp microscope 4. The laser beam is focused on the affected part in the fundus of the patent's eye after being reflected by the dichroic mirror 11 to perform photocoagulation on the affected part.

During the ophthalmic operation by photocoagulation using the above apparatus, an oculist observes the patient's eye 13 through the dichroic mirror 11 by the slit-lamp microscope 4. However, because of a very narrow distance between inherent objective plane 14 (focused plane) in the slit-lamp microscope 4 and the housing 3 of the laser optical system, it is necessary to obtain a working distance between the laser optical system and the patient's eye 13. This is accomplished by arranging a concave lens 15 on the light path of the observing system to shift the objective plane 14 to the position indicated by numeral 16.

More specifically, the position indicated by numeral 16 is located slightly at the right side, toward the slit-lamp microscope 4 due to the effect of refractive indices of both the patient's eye 13 and the medium of the contact lens 12. Further, the concave lens 15 is arranged to be inclined against the optical axis of illuminating light source 17 to prevent light reflected by the concave lens 15 from entering into the visual field of the observing system since illumination of the patient's eye 13 is conducted by the illuminating light source 17.

The edge plane 18 of the optical fiber 2 and the new objective plane 16 formed by the arrangement of the concave lens 15 are mutually conjugated through the lenses 6, 9 and 10. Therefore, the laser beam is focused on the fundus of the patient's eye 13 when the visual field of the observing system is focused on the fundus of the patient's eye 13 by adjusting the position of the slit-lamp microscope 4.

As described above, ophthalmic treatment by the laser beam is conducted while the contact lens 12 is placed over the patient's eye 13. Two types of contact lenses are used during the ophthalmic treatment. FIG. 8 shows an embodiment using a first type of contact lens 12.

In FIG. 9(a), the optical characteristics of the first type of contact lens 12 are shown. The laser beam reflected by the dichroic mirror 11 is focused on the fundus of the patient's eye 13 through the first type of contact lens 12. The first type of contact lens 12 is formed by cutting a cone body made of glass or acrylic resin so that the part of the lens 12 contacting the patient's eye 13 has a concave shape with a curvature the same as the curvature of the cornea of the patient's eye 13. By having the concave shape of the lens 12 contact the cornea of the patient's eye 13, an underserved effect caused by the refracting power of the cornea is prevented. Thus, the laser beam reflected by the dichroic mirror 11 is approximately aligned toward the fundus of the patient's eye 13 through the first type of contact lens 12.

In FIG. 9(b), the optical characteristics of a second type contact lens 12' is shown. This type of contact lens is more widely used than the first type of contact lens 12 in ophthalmic treatments. The second type of contact lens 12' focuses the fundus image of the patient's eye 13 on a plane 20 located in front of the patient's eye 13 and is advantageously capable of observing a fundus area that is wider than the first type of contact lens 12 based on the optical characteristics.

When the second type of contact lens 12' is used instead of the first type of contact lens 12 in the apparatus shown in FIG. 8, it is necessary to move the objective plane 16 to the plane 20 because the second type of contact lens 12' focuses the fundus image on the plane 20. Accordingly, the slit-lamp microscope 4 should be directed away from the patient's eye 13, in order to have the objective plane 16 coincide with the plane 20, because the patient's head 23 is substantially fixed to a headrest 22 and the headrest 22 is fixed to a table 21 on which the slit-lamp microscope 4 is mounted.

However, the movable range of the slit-lamp microscope 4 on the table 21 is very limited. Thus, an oculist is not able to keep the slit-lamp microscope 4 sufficiently from the patient's eye 13 in addition to the condition that the newly set objective plane 16 is moved from the objective plane 14, inherent in the slit-lamp microscope 4, by providing the concave lens 15 in the optical axis of the observing system, as described above. As a result, an oculist is not able to observe the fundus of the patient's eye 13.

To resolve this problem, it is possible to shorten the distance along which the new objective plane 16 is to be moved from the inherent objective plane 14, by weakening the refracting power of the concave lens 15. However, if the distance is shortened to an extent such that the second type of contact lens 12' becomes usable for the apparatus, the first type of contact lens 12 may not be usable because the space between the first contact lens 12 and the housing 3 of the laser optical system may become too small.

It is also possible to compensate for the limited movable range of the slit-lamp microscope 4 by modifying the connecting part between the headrest 22 and the table 21 to be movable in an opposite direction from the slit-lamp microscope 4. However, to realize this modification, it will be necessary to change the basic system of the slit-lamp microscope 4, and as a result, the slit-lamp microscope system will become structurally complex and cost-consuming.

Further, it is conceivable to provide a convex lens 24 at a position where the laser beam light path and the observing light path become coaxial for the second type of contact lens 12', as shown in FIG. 10. The convex lens 24 will compensate for the limited movable range of the slit-lamp microscope 4 by moving the new objective plane 16 toward the slit-lamp microscope 4. However, it would be very difficult to observe precisely the fundus of the patient's eye 13 because the reflected light from the convex lens 24 will enter the observed visual field, unless the convex lens 24 is arranged in an inclined or eccentric position against both the laser beam light path and the observing light path. In addition, a spot laser beam that is sufficiently small for use in the ophthalmic treatment of the fundus cannot be obtained because of a lens defect such as coma aberration, that is added to the laser beam light path when the convex lens 24 is arranged in the inclined or eccentric position.

Similar problems, as discussed above, exist when using the first type of contact lens 12 in an apparatus that is designed around the second type of contact lens 12'.

SUMMARY OF THE INVENTION

The present invention has been made in view of the above circumstances and has as an object of overcoming the above mentioned problems.

Another object of the present invention is to provide an apparatus for selectively using the above first and second types of contact lenses for efficiently performing ophthalmic operations.

To achieve the objects and in accordance with the purpose of the invention, as embodied and broadly described herein, the apparatus for performing an ophthalmic operation on an eye by photocoagulation using a laser beam while allowing continuous observation of the eye to be treated comprises a light source for producing the laser beam, an observing system having a first inherent optical path including a slit-lamp microscope, a laser optical system having a second inherent optical path, means for transmitting the laser beam from the light source to the laser optical system, means for introducing the laser beam from the second optical path of the laser optical system to the first optical path of the observing system, first optical means provided in the first inherent optical path of the observing system for adjusting an objective plane observable from the slit-lamp microscope, means for shifting the objective plane to a desired position along the optical path while observing the objective plane, and second optical means provided in the second inherent optical path of the laser optical system for adjusting a focal point, the laser beam being controlled while adjusting the focal point along the second optical path of the laser optical system, wherein the laser beam is directed on the objective plane by operating the first optical means in conjunction with the second optical means.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification illustrate embodiments of the invention and, together with the description, serve to explain the objects, advantages and principles of the invention.

In the drawings.

DETAILED DESCRIPTION OF THE PREFERRED EMBODIMENTS

A detailed description of the first preferred embodiment of an apparatus for performing an ophthalmic operation using photocoagulation by a laser beam of the present invention will be given referring to the accompanying drawings.

Figure 1:
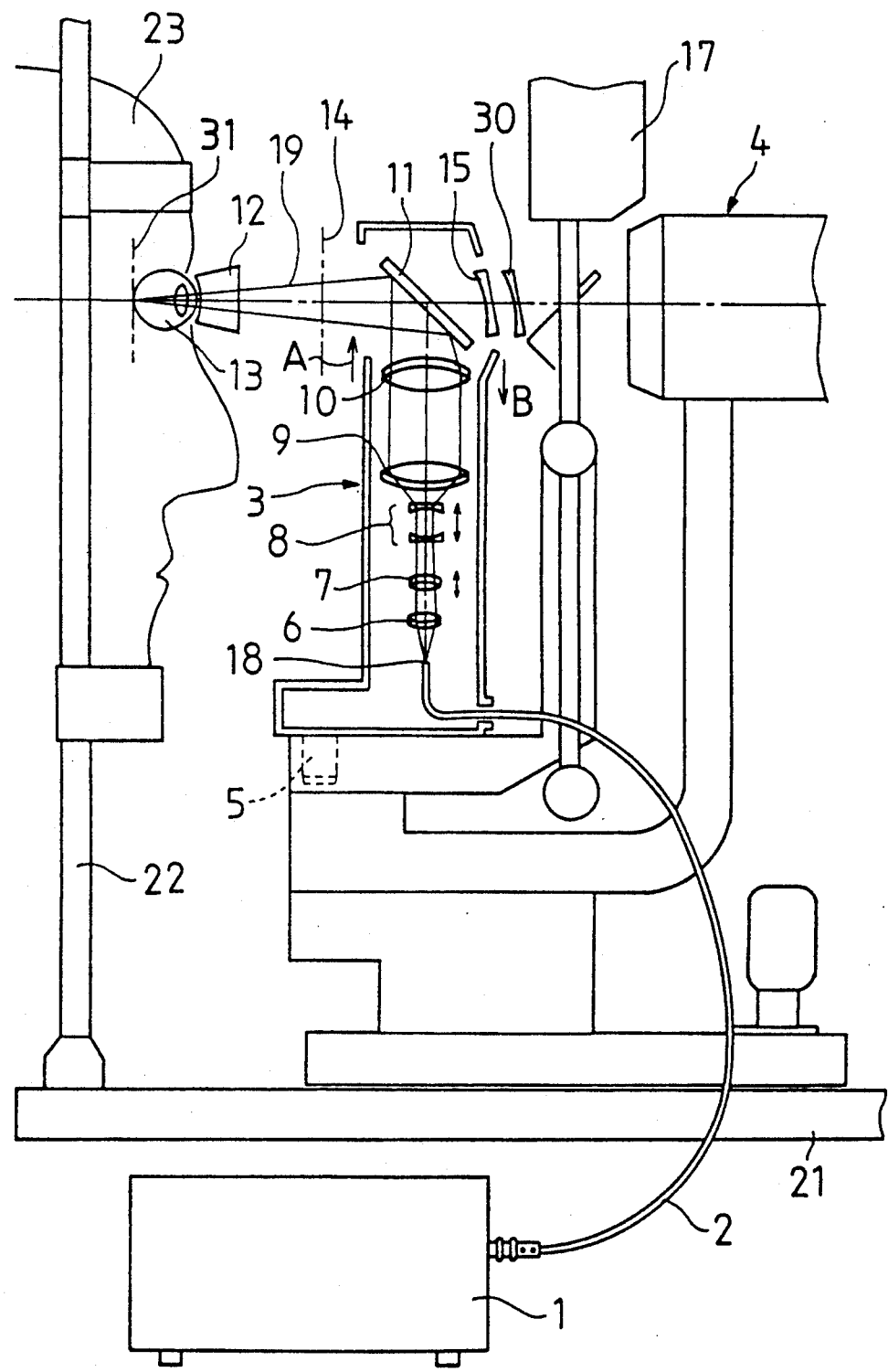
FIG. 1 is a schematic view of the apparatus of the present invention using a first type of contact lens, according to a first embodiment of the present invention.
Figure 8:
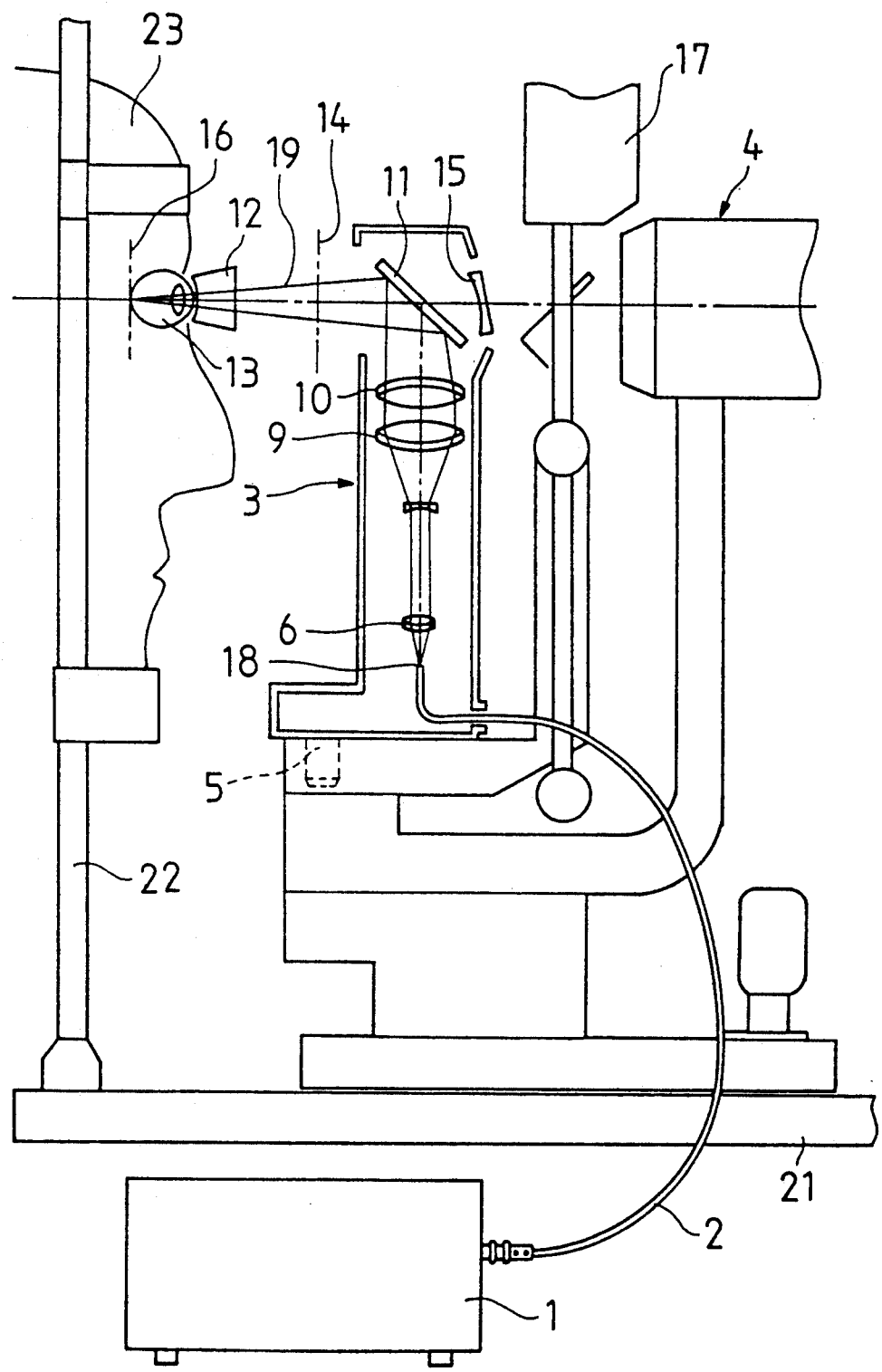
FIG. 8 is a schematic view of a conventional apparatus for performing an ophthalmic operation using photocoagulation by a laser beam.
Figure 9A:
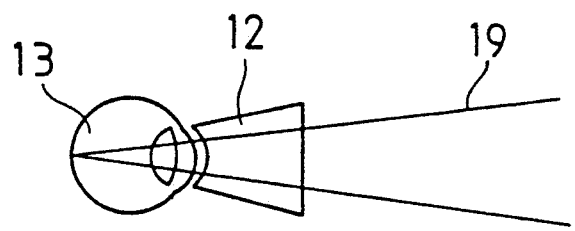
FIG. 9(a) and FIG. 9(b) are schematic views for explaining the optical characteristics of both the first type of contact lens and the second type of contact lens.
Figure 9B:
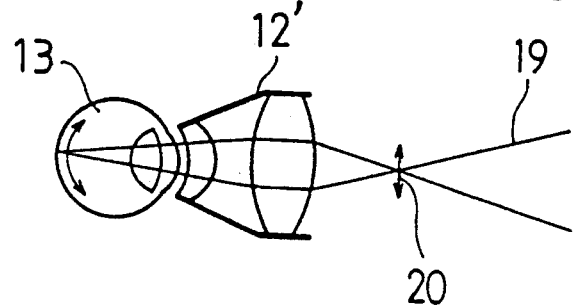
Figure 10:
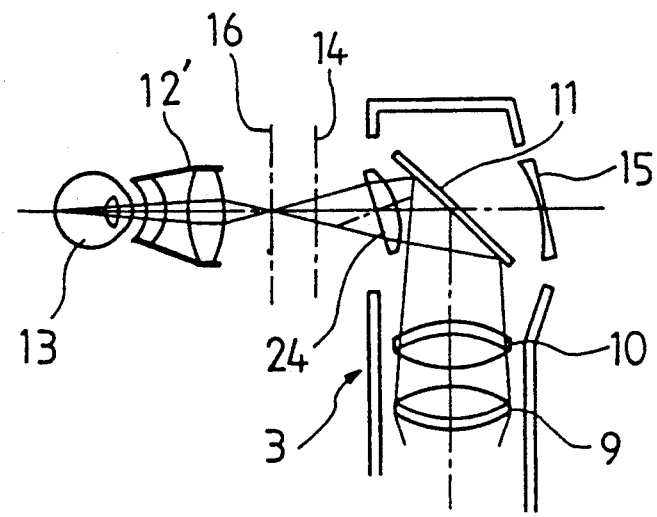
FIG. 10 is a schematic view of the laser optical system in which the convex lens is in an inclined position in the apparatus of FIG. 8.

The apparatus according to the first embodiment shown in FIG. 1 has a basic construction similar to the conventional apparatus, as discussed above with reference to FIG. 8. Thus, the detailed description of each element of the first embodiment that is similar to the conventional apparatus will be omitted.

In FIG. 1, a concave lens 30 is movably provided at a first position, where the optical axis of the concave lens 30 is aligned with the optical axis of the observing system including the slit-lamp microscope 4, or at a second position (see FIG. 2), where the optical axis of the concave lens 30 is not aligned with the optical axis of the observing system.

Further, lens 10, positioned in the housing 3 of the laser optical system, is made movable along the optical axis of the laser optical system. In FIG. 1, arrow A indicates that lens 10 is moved to a position closer to the patient's eye 13 than a normal position.

The lenses 7 and 8 in the housing 3 of the laser optical system are designed to be mutually movable by a well-known cam mechanism. Hence, the laser optical system has a zooming capability. As a result, an oculist can continuously change the projection magnification of the laser beam emitted from the edge plane 18 of the optical fiber 2 on the fundus of the patient's eye 13. Therefore, an oculist can continuously change the laser beam spot size projected on the fundus of the patient's eye 13.

The laser optical system is designed to be able to obtain a substantially parallel luminous flux between lens 9 and lens 10. Thus, the laser beam emitted from the edge plane 18 can be projected on the fundus without changing the laser beam spot size even if lens 10 is moved.

Next, referring to FIG. 3(a), a driving mechanism DM1 for driving the concave lens 30 and lens 10 will be described.

Two shafts 50 and 51 are fixedly positioned between mounting bases B1 and B2. The concave lens 30 is mounted in a lens holder 52 and a throughhole 53 for receiving the shaft 51 is formed at the right side of the lens holder 52.

A horizontal plate 54 having a throughhole 55 is attached on the left side plane of the lens holder 52. The shaft 50 is inserted in the throughhole 55 and a compression spring 56 is arranged around the shaft 50 between the horizontal plate 54 and the mounting base B1.

It should be clear from the above description that the lens holder 52 can be slidably guided in both upward and downward directions by the shaft 50, which is inserted in the throughhole 55, and by the shaft 51, which is inserted in the throughhole 53.

One end of a pushing rod 57 is fixed on a lower plane of the horizontal plate 54 and the other end thereof contacts a side edge of a rack plate 58 having gear mesh teeth 58A. A first pinion gear 59, which is fixed to one end of a gear shaft 60, is meshed with the gear mesh teeth 58A of the rack plate 58. At the other end of the gear shaft 60, a rotational knob 61 is fixed and, at the middle of the gear shaft 60, a second pinion gear 62 is fixed. The knob 61 can be rotated with the gear shaft 60.

Figure 2:
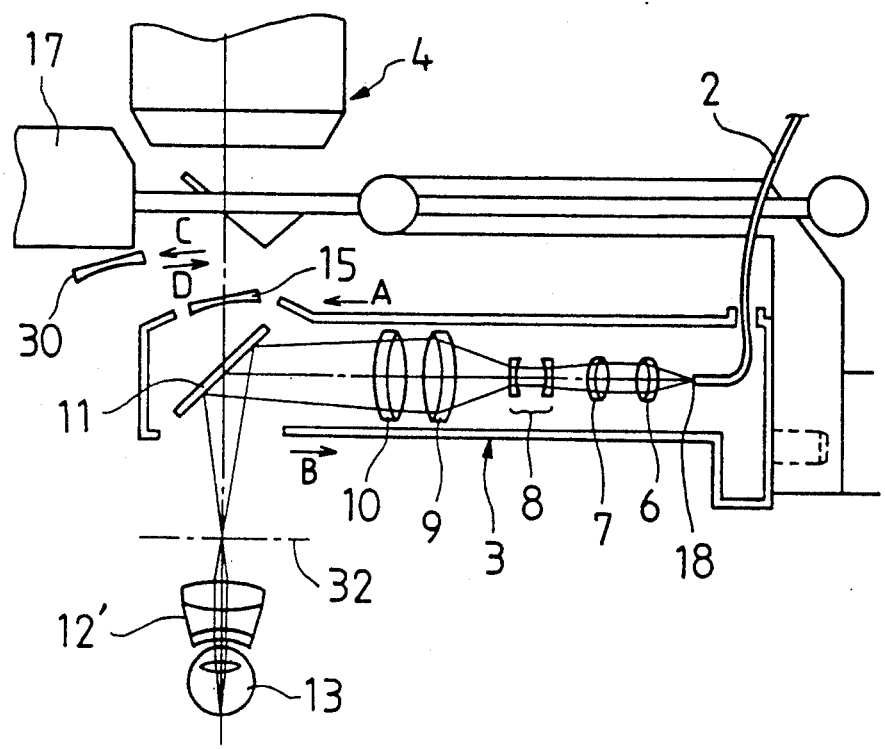
FIG. 2 is a fragmentary schematic view of the observing system and laser optical system in the apparatus of FIG. 1, using a second type of contact lens.

The lens 10 is mounted in a cylindrical lens holder 63. A rack part 64 having gear mesh teeth 65 is formed on a circumferential part of the lens holder 63 so that the gear mesh teeth 65 mesh with the pinion gear 62. Therefore, when the knob 61 is rotated in the direction indicated by an arrow E, the lens holder 63 is moved downward in the direction indicated by an arrow B because the pinion gear 62 fixed to the gear shaft 60 drives the rack part 64 downward. Accordingly, lens 10 is moved toward the lens 9 in FIG. 1. Further, as the pinion gear 59 is also rotated in the direction E, the rack plate 58 is moved upward in the direction indicated by an arrow G. As a result, the pushing rod 57 forces the horizontal plate 54 upward against the force of the compression spring 56, thus, the lens holder 52 is moved upward in the direction indicated by an arrow D. Accordingly, the concave lens 30 is placed at the second position, as shown in FIG. 2.

On the other hand, when the knob 61 is rotated in the opposite direction as indicated by an arrow F, the lens holder 63 is moved upward in the direction indicated by an arrow A and the lens holder 30 is moved downward in the direction indicated by an arrow C based on reverse actions of the second pinion gear 62, the first pinion gear 59, the rack plate 58, the pushing rod 57, and the compression spring 56. Thus, the concave lens 30 is placed at the first position as shown in FIG. 1. Also, lens 10 is moved away from lens 9.

Therefore, when an oculist uses the first type of contact lens 12, the knob 61 is rotated in the direction F. As a result, the concave lens 30 is placed at the first position where the optical axis of the concave lens 30 is aligned with the optical axis of the observing system and lens 10 is separated at a longer distance from lens 9, as shown in FIG. 1. Accordingly, the objective plane 14, inherent in the slit-lamp microscope 4 of the apparatus, can be separated sufficiently from the housing 3 of the laser optical system by inserting the concave lens 30 in the optical axis of the observing system in addition to the concave lens 15. Thus, sufficient distance between the first type of contact lens 12 and the housing 3 of the laser optical system can be obtained. Additionally, lens 10 in the laser optical system is moved toward the patient's eye 13 and the laser beam is focused on the new objective plane 31, as shown in FIG. 1.

On the other hand, when an oculist uses the second type of contact lens 12', the knob 61 is rotated in the direction E. As a result, the concave lens 30 is placed at the second position where the optical axis of the concave lens 30 is not aligned with the optical axis of the observing system and lens 10 is moved closely towards lens 9, as shown in FIG. 2. Accordingly, the objective plane 14, inherent in the slit-lamp microscope 4, is positioned close to the housing 3 of the laser optical system. Thus, the limited movable range in the slit-lamp microscope 4 is compensated. Also, in the laser system, the laser beam reflected by the dichroic mirror 11 is focused onto the new objective plane 32 since lens 10 is moved close to lens 9, as shown in FIG. 2. Thus, the laser beam is focused onto the fundus of the patient's eye 13 through the second type of contact lens 12'.

Figure 3A:
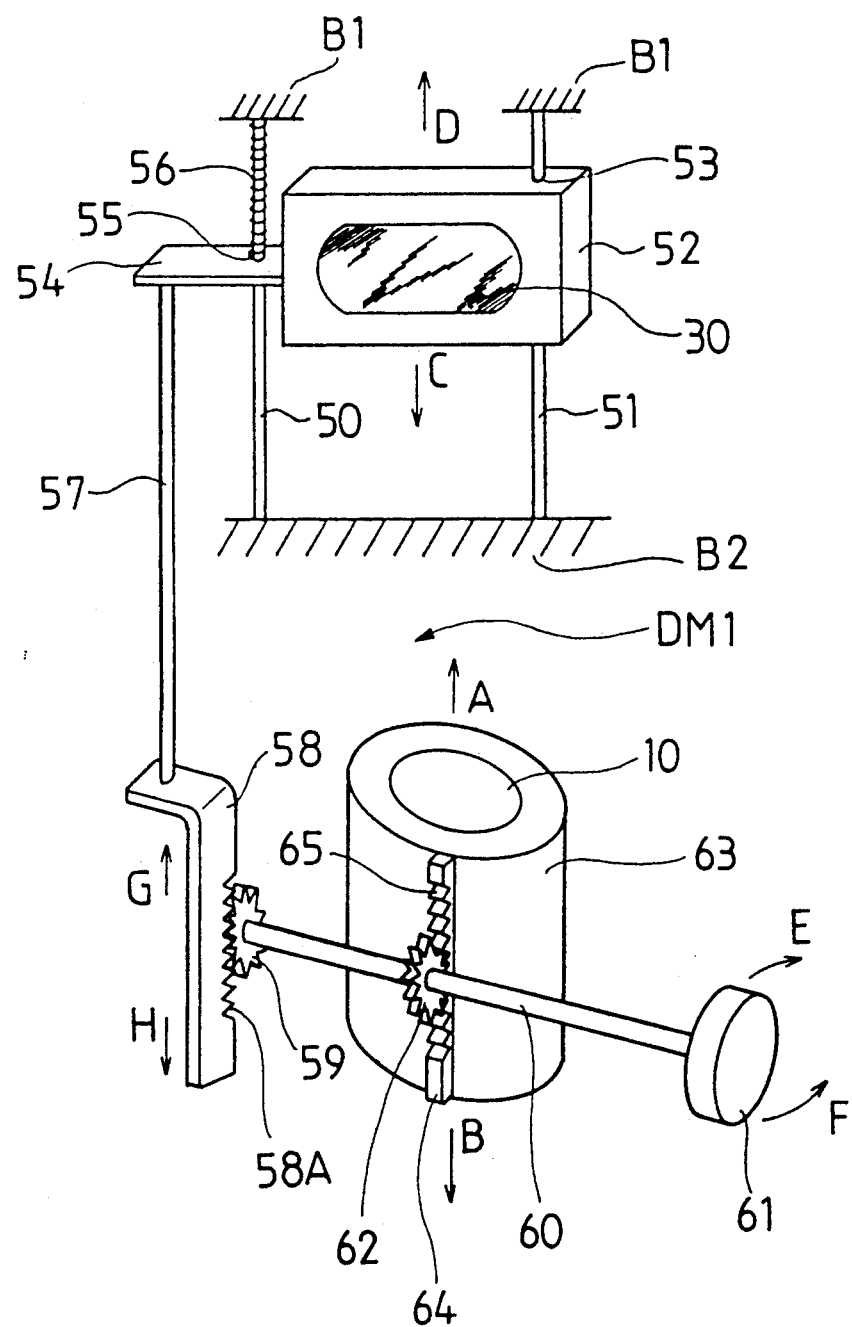
FIG. 3(a) and FIG. 3(b) are fragmentary schematic views of a driving mechanism for driving both the concave lens arranged in the observing system and lens arranged in the laser optical system, in the apparatus of FIG. 1.
Figure 3:
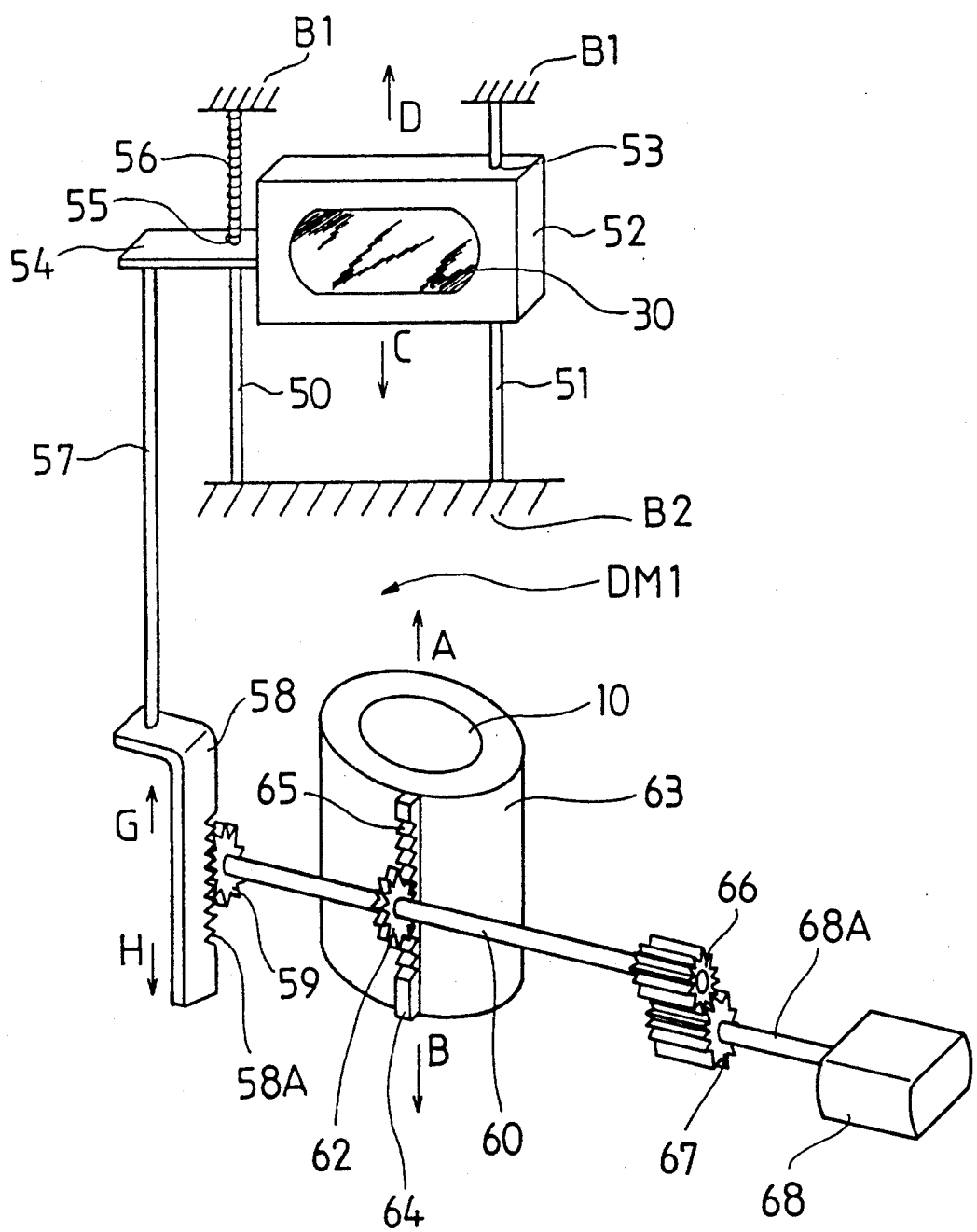

As discussed above, although the concave lens 30 and lens 10 are manually moved by rotating the knob 61 in the first embodiment, the gear shaft 60 may be rotated by a driving motor such as a stepping motor, as shown in FIG. 3(b). In FIG. 3(b), a pinion gear 66 is fixed to an end of the gear shaft 60 opposite the pinion gear 59 and is meshed with a pinion gear 67 which is fixed to a drive shaft 68A of a driving motor 68. According to this construction, the lens holder 63 of lens 10 and the lens holder 52 of the concave lens 30 are moved in a similar manner as described above referring to FIG. 3(a), but in accordance with normal and reverse rotations of the driving motor 68.

The second preferred embodiment of the present invention will be described referring to FIGS. 4, 5 and 6. The apparatus according to the second embodiment also has a construction similar to the conventional apparatus. Thus, detailed description of each element similar to the conventional apparatus will be omitted.

In the apparatus according to the second embodiment, a concave lens 33 is movably provided at one of two positions, similar to the concave lens 30 of the first embodiment. Therefore, the optical axis of the concave lens 33 is aligned with the optical axis of the observing system at the first position and is not aligned with the optical axis of the observing system at the second position. In FIG. 4, the concave lens 33 is positioned at the first position, and in FIG. 5, the concave lens 33 is positioned at the second position. The function of the concave lens 33 is the same as the function of the concave lens 30 of the first embodiment.

Figure 4:
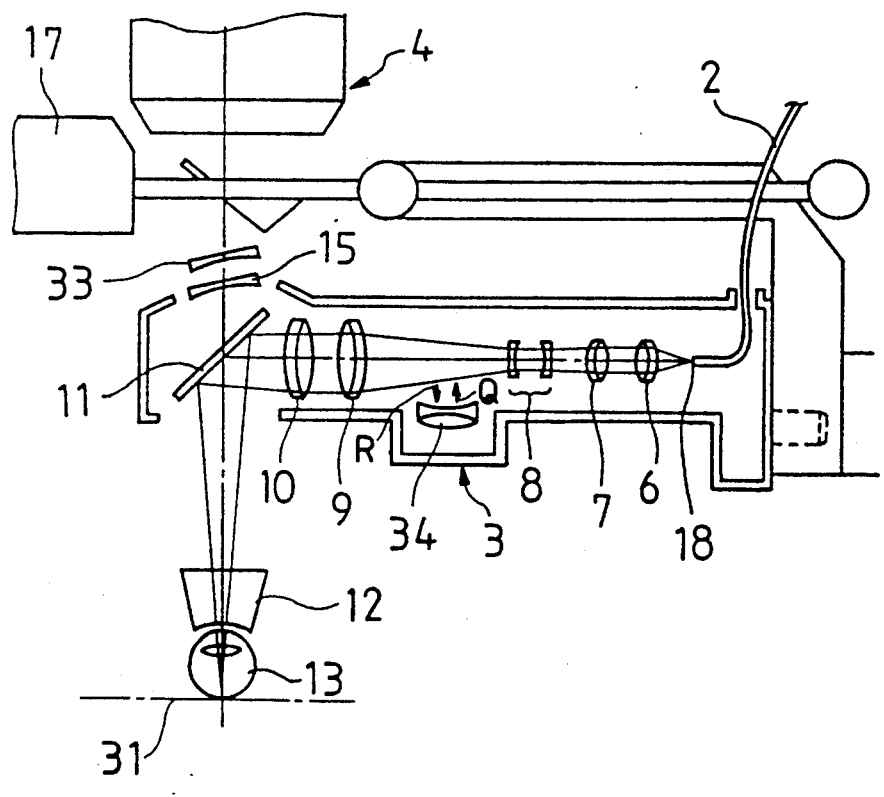
FIG. 4 is a fragmentary schematic view of the observing system and laser optical system according to a second embodiment of the present invention, using the first type of contact lens.
Figure 5:
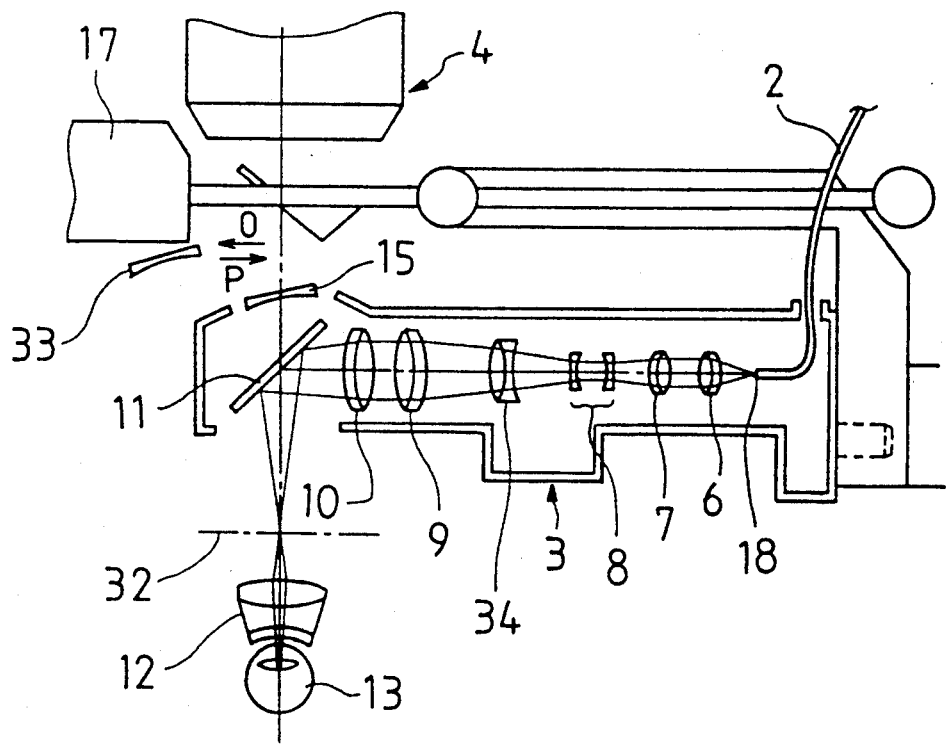
FIG. 5 is a fragmentary schematic view of the observing system and laser optical system in the apparatus of FIG. 3, using the second type of contact lens.

In addition to the concave lens 33, a convex lens 34 is movably provided at a first position where the convex lens 34 is not aligned with the optical axis of the laser optical system (FIG. 4) and at a second position where the convex lens 34 is aligned with the optical axis of the laser optical system (FIG. 5). This convex lens 34 focuses the laser beam, inherent in the observing system, on a new objective plane 31 if at the first position when the first type of contact lens 12 is used, and focuses the laser beam reflected by the dichroic mirror 11 onto the new objective plane 32 if at the second position when the second type of contact lens 12' is used (to be described later).

Figure 6:
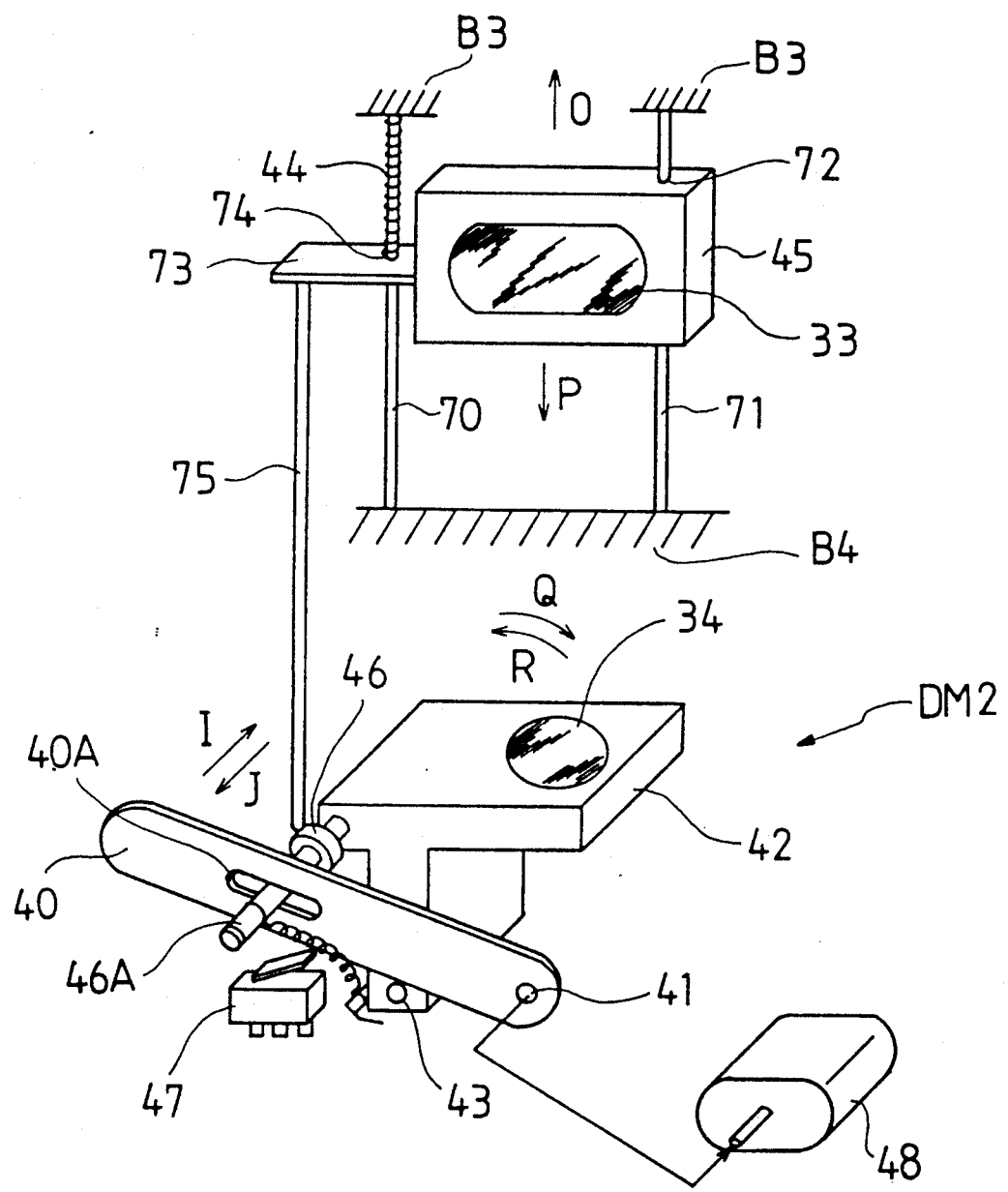
FIG. 6 is a fragmentary schematic view of the driving mechanism for driving both the concave lens arranged in the observing system and the convex lens arranged in the laser optical system in the apparatus of FIG. 4.

Referring to FIG. 6, a driving mechanism DM2 for driving the concave lens 33 and the convex lens 34 will be described.

Two shafts 70 and 71 are fixedly positioned between mounting bases B3 and B4. The concave lens 33 is mounted in a lens holder 45 and a throughhole 72 for inserting shaft 71 is formed at the right side of the lens holder 45.

A horizontal plate 73 having a throughhole 74 is attached on the left side plane of the lens holder 45. The shaft 70 is inserted in the throughhole 74 and a compression spring 44 is arranged around the shaft 70 between the horizontal plate 73 and the mounting base B3.

It should be clear from the above description that the lens holder 45 can be slidably guided in both upward and downward directions through the shaft 70, which is inserted in the throughhole 73, and the shaft 71, which is inserted in the throughhole 72.

One end of a pushing rod 75 is fixed on a lower plane of the horizontal plate 73 and the other end thereof contacts a bearing 46 on a bearing shaft 46A. One end of the bearing shaft 46A is connected to a side plane of a lens holder 42 having a T shape and in which the convex lens 34 is mounted. The lens holder 42 is rotatably supported on a supporting shaft 43. The other end of the bearing shaft 46A is slidably inserted into an elongated aperture 40A formed in an exchanging lever 40. The exchanging lever 40 is rotatably supported on a supporting shaft 41 toward the directions indicated by an arrow I and J in FIG. 6. The supporting shaft 41 is connected to a driving motor 48 such as a step motor and is rotated so as to rotate the exchanging lever 40 in the direction I and J according to normal and reverse rotations of the driving motor 48.

Further, a detecting switch 47 for detecting downward motions of the bearing 46 is positioned under the bearing 46. Based on the switching signal output from the detecting switch 47, the visual field of the slit-lamp microscope 4 displays whether the objective plane 14 is changed to either the new objective plane 31 or 32 and, if necessary, the laser beam spot size is adjusted.

Therefore, when the exchanging lever 40 is rotated in the direction indicated by the arrow J by the driving motor 48, the lens holder 42 is rotated in the direction indicated by an arrow R through the connection between the elongated aperture 40A and bearing shaft 46A. As a result, the convex lens 34 is positioned at the first position where the optical axis of the convex lens 34 is not aligned with the optical axis of the laser optical system. At the same time, the lens holder 45 is moved downward in the direction indicated by an arrow P in response to a downward motion of the bearing 46 which contacts the free end of the pushing rod 75. Accordingly, the concave lens 33 is placed at the first position where the optical axis of the concave lens 33 is aligned with the optical axis of the observing system.

On the other hand, when the exchanging lever 40 is rotated in the direction indicated by the arrow I by the driving motor 48, the lens holder 42 is rotated in the direction indicated by an arrow Q through the connection between the elongated aperture 40A and the bearing shaft 46A. As a result, the convex lens 34 is positioned at the second position where the optical axis of the convex lens 34 is aligned with the optical axis of the laser optical system. At the same time, the lens holder 45 is moved upward in the direction indicated by an arrow 0 through an upward force transmitted by the bearing 46 on the pushing rod 75, the horizontal plate 73, and the compressing spring 44, in accordance with the rotation of the lens holder 42 in the direction Q.

Therefore, when an oculist applies the first type of contact lens 12, the exchange lever 40 is rotated in the direction J. As a result, the concave lens 33 is placed at the first position where the optical axis of the concave lens 33 is aligned with the optical axis of the observing system and where the convex lens 34 is not aligned with the optical axis of the laser optical system, as shown in FIG. 4. Accordingly, the objective plane 14, inherent in the observing system of the apparatus, can be separated sufficiently from the housing 3 of the laser optical system by inserting the concave lens 33 in the optical axis of the observing system in addition to the concave lens 15. Thus, sufficient distance between the first type of contact lens 12 and the housing 3 of the laser optical system can be obtained. Additionally, the laser beam is focused on the new objective plane 31, as shown in FIG. 4.

On the other hand, when an oculist applies the second type of contact lens 12', the exchange lever 40 is rotated in the direction I. As a result, the concave lens 33 is placed at the second position where the optical axis of the concave lens 33 is not aligned with the optical axis of the observing system and where the convex lens 34 is aligned with the optical axis of the laser optical system, as shown in FIG. 5. Accordingly, the objective plane 14 is positioned close to the housing 3 of the laser optical system. Thus, the limited movable range in the slit-lamp microscope 4 is compensated. Also, in the laser system, the laser beam reflected by the dichroic mirror 11 is focused onto the new objective plane 32 since the convex lens 34 is aligned with the optical axis of the laser optical system, as shown in FIG. 5. Thus, the laser beam is focused onto the fundus of the patient's eye 13 through the second type of contact lens 12'.

It is preferable that the convex lens 34 is positioned between lens 8 and lens 9, as shown in FIGS. 4 and 5, since difference of the spot size on the fundus of the patient's eye 13 between the first and the second position of the convex lens 34 can be reduced when the laser beam emitted from the edge plane 18 is focused on the fundus of the patient's eye 13. The convex lens 34 may be positioned between lens 10 and the dichroic mirror 11, for example. However, it may be necessary to adjust the laser beam spot size displayed on the visual field of the slit-lamp microscope 4 if the projection magnification difference of the laser beam spot focused on the fundus of the patient's eye 13 is large.

Figure 7:
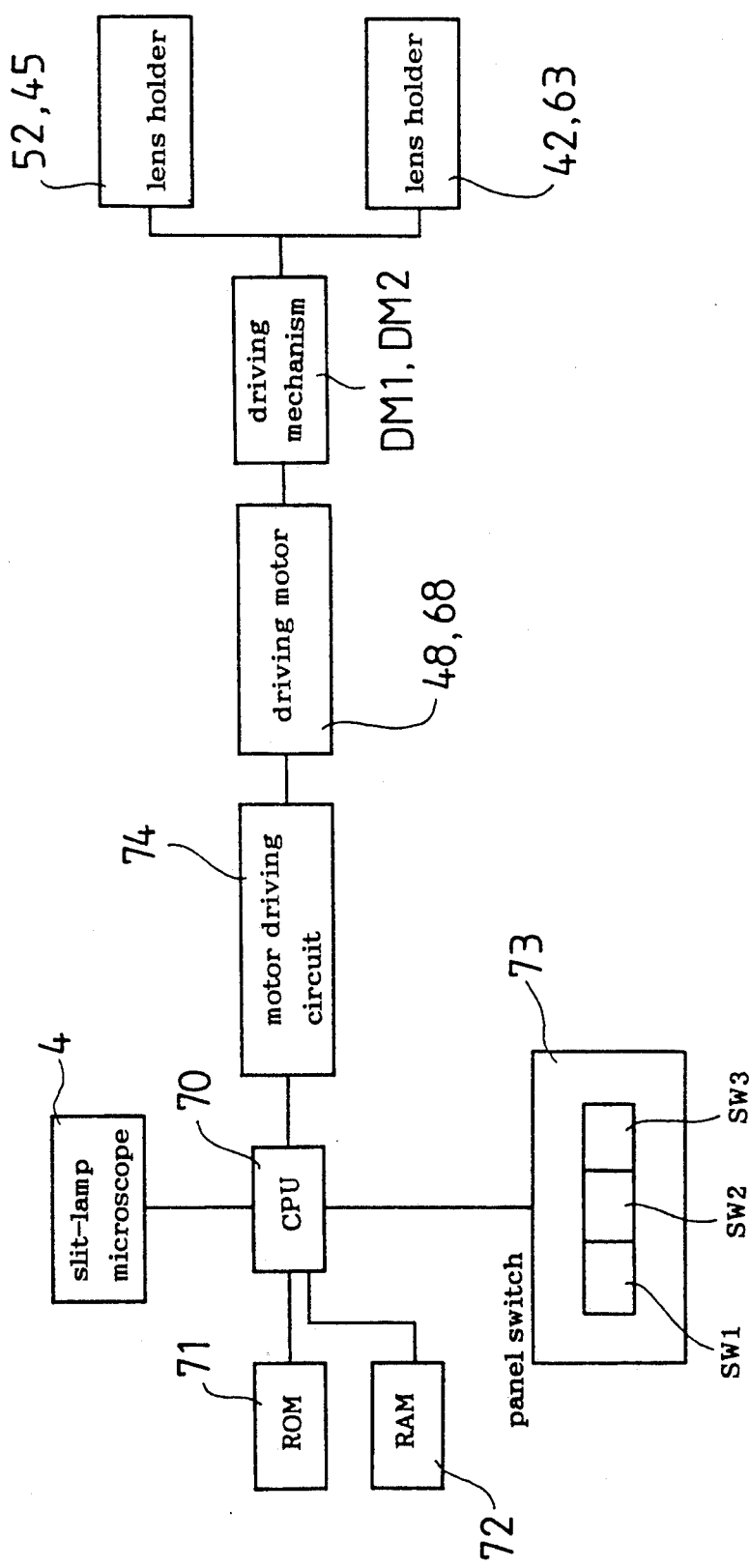
FIG. 7 is a block diagram for controlling the first embodiment and the second embodiment of the present invention.

Now, referring to FIG. 7, a control system for controlling the apparatus of the first and second embodiments will be described. The apparatus is controlled mainly by CPU 70 which includes ROM 71 and RAM 72. The CPU 70 conducts various calculations based on a control program stored in the ROM 71 and stores the calculated results in the RAM 72. A panel switch 73 having three switches (SW1, SW2 and SW3) is connected to the CPU 70. Switch SW1 is a starting switch for activating the apparatus and switches SW2 and SW3 are selective switches for selecting a mode for choosing either the first type of contact lens 12 or the second type of contact lens 12'. Specifically, selective switch SW2 selects the mode for the first type of contact lens 12 and selective switch SW3 selects the mode for the second type of contact lens 12'.

The slit-lamp microscope 4 is connected to the CPU 70 which controls displaying of informations such as the laser beam spot size and change of the objective plane displayed on the visual field of the slit-lamp microscope 4. Further, motor driving circuit 74 and driving motors 68, 48 are connected to the CPU 70. Thus, while being controlled by the CPU 70, the motor driving circuit 74 drives the driving motors 68, 48, and as a result, the driving mechanisms DM1, DM2 move the lens holders 52, 63 and 42, 45, respectively, as discussed above.

Accordingly, when an oculist intends to start the ophthalmic treatment on the fundus of the patient's eye 13, the starting switch SW1 is pressed to activate the apparatus. Selective switches SW2 and SW3 are pressed according to the contact lens (12 or 12') to be used, where selective switch SW2 corresponds to the contact lens 12 and selective switch SW3 corresponds to the contact lens 12'.

The CPU 70 drives the driving motors 68, 48 by the motor driving circuit 74 based on the switching signal from the selective switches SW2 and SW3, according to the control program stored in the ROM 71. As a result, the driving mechanisms DM1, DM2 are driven by the driving motors 68, 48 to move the lens holders 52, 63 and 42, 45, respectively.

While the invention has been shown and described with reference to preferred first and second embodiments thereof, it will be understood by those skilled in the art that the foregoing and other changes can be made therein without departing from the spirit and scope of the invention.

For example, the second embodiment can be constructed such that the concave lens 33 of the observing system may be replaced by a convex lens which is aligned with the optical axis of the observing system when the second type of contact lens 12' is used, and the convex lens 34 of the laser optical system may be replaced by a concave lens which is aligned with the optical axis of the laser optical system when the first type of contact lens 12' is used. Also, the lens of the observing system may move along the optical axis of the observing system instead of being aligned or not aligned with the optical axis of the observing system.

The foregoing description of preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for performing an ophthalmic operation on an eye by photocoagulation using a laser beam while allowing continuous observation of the eye to be treated, comprising:
   a light source for producing the laser beam;
   an observing system having a first optical path including a slit-lamp microscope;
   a laser optical system having a second optical path;
   means for transmitting said laser beam from said light source to said laser optical system;
   means for introducing the laser beam from said second optical path of said laser optical system to said first optical path of said observing system;
   first optical means provided in said first optical path of said observing system for adjusting an objective plane observable from said slit-lamp microscope; and
   second optical means provided in said second optical path of said laser optical system for adjusting a focal point of said laser beam from said light source, said laser beam being controlled while adjusting said focal point along said second optical path of the laser optical system;
   wherein said laser beam is focused on said objective plane by operating said first optical means in conjunction with said second optical means;
   wherein said first optical means is a movable lens capable of movement into and out of alignment with the first optical path of the observing system.

2. The apparatus according to claim 1, further comprising driving means for driving at least one of the first and second optical means.

3. The apparatus according to claim 1, wherein said laser beam is selected from one of a low power laser beam and a high power laser beam.

4. An apparatus for performing an ophthalmic operation on an eye by photocoagulation using a laser beam while allowing continuous observation of the eye to be treated, comprising:
   a light source for producing the laser beam;
   an observing system having a first optical path including a slit-lamp microscope;
   a laser optical system having a second optical path;
   means for transmitting said laser beam from said light source to said laser optical system;
   means for introducing the laser beam from said second optical path of said laser optical system to said first optical path of said observing system;
   first optical means provided in said first optical path of said observing system for adjusting an objective plane observable from said slit-lamp microscope; and
   second optical means provided in said second optical path of said laser optical system for adjusting a focal point of said laser beam from said light source, said laser beam being controlled while adjusting said focal point along said second optical path of the laser optical system;

wherein said laser beam is focused on said objective plane by operating said first optical means in conjunction with said second optical means;

wherein said second optical means is a movable lens capable of movement into and out of alignment with the second optical path of the laser optical system.

5. The apparatus according to claim 4, further comprising driving means for driving at least one of the first and second optical means.

6. The apparatus according to claim 4, wherein said laser beam is selected from one of a low power laser beam and a high power laser beam.

7. The apparatus according to claim 4, further comprising a contact lens having predetermined characteristics positioned in front of and contacting the eye to be treated;

wherein said first optical means controls the movement of the objective plane observed by said observing system according to said predetermined characteristics of said contact lens and said second optical means adjusts the focal point to focus the laser beam on the objective plane.

8. The apparatus according to claim 7, wherein said contact lens has an optical characteristic to allow an image of a fundus of the eye to be focused on a plane in front of the eye.

9. The apparatus according to claim 7, wherein said contact lens has an optical characteristics to prevent refracting power from the cornea of the eye to be treated and to allow an image of a fundus of the eye to be observed.

10. An apparatus for performing an ophthalmic operation on an eye by photocoagulation using a laser beam while allowing continuous observation of the eye to be treated, comprising:

a light source for producing the laser beam;
an observing system having a first optical path including a slit-lamp microscope;
a laser optical system having a second optical path;
means for transmitting said laser beam from said light source to said laser optical system;
means for introducing the laser beam from said second optical path of said laser optical system to said first optical path of said observing system;
first optical means provided in said first optical path of said observing system for adjusting an objective plane observable from said slit-lamp microscope; and
second optical means provided in said second optical path of said laser optical system for adjusting a focal point of said laser beam from said light source, said laser beam being controlled while adjusting said focal point along said second optical path of the laser optical system;
wherein said laser beam is focused on said objective plane by operating said first optical means in conjunction with said second optical means;
wherein said second optical means is a lens movable along the second optical path of the laser optical system.

11. The apparatus according to claim 10, wherein the laser optical system comprises means for irradiating said lens with said laser beam;
said laser beam being parallel to said second optical path.

12. The apparatus according to claim 10, further comprising driving means for driving at least one of the first and second optical means.

13. The apparatus according to claim 10, wherein said laser beam is selected from one of a low power laser beam and a high power laser beam.

14. An apparatus for performing an ophthalmic operation on an eye by photocoagulation using a laser beam while allowing continuous observation of the eye to be treated, comprising:

a light source for producing the laser beam;
an observing system having a first optical path including a slip-lamp microscope;
a laser optical system having a second optical path;
means for transmitting said laser beam from said light source to said laser optical system;
means for introducing the laser beam from said second optical path of said laser optical system to said first optical path of said observing system;
a contact lens having predetermined characteristics positioned in front of and contacting the eye to be treated;
first optical means provided in said first optical path of said observing system for adjusting an objective plane observable from said slit-lamp microscope; and
second optical means provided in said second optical path of said laser optical system for adjusting a focal point, said laser beam being controlled while adjusting said focal point along said second optical path of the laser optical system;
wherein said first optical means controls the movement of the objective plane observed by said observing system according to said predetermined characteristics of said contact lens and said second optical means adjusts the focal point to focus the laser beam on the objective plane;
wherein said first optical means is a movable lens capable of movement into and out of alignment with the first optical path of the observing system.

15. The apparatus according to claim 14, wherein said contact lens has an optical characteristic to allow an image of a fundus of the eye to be focused on a plane in front of the eye.

16. The apparatus according to claim 14, wherein said contact lens has an optical characteristic to prevent refracting power from the cornea of the eye to be treated and to allow an image of a fundus of the eye to be observed.

17. An apparatus for performing an ophthalmic operation on an eye by photocoagulation using a laser beam while allowing continuous observation of the eye to be treated, comprising:

a light source for producing the laser beam;
an observing system having a first optical path including a slip-lamp microscope;
a laser optical system having a second optical path;
means for transmitting said laser beam from said light source to said laser optical system;
means for introducing the laser beam from said second optical path of said laser optical system to said first optical path of said observing system;
a contact lens having predetermined characteristics positioned in front of and contacting the eye to be treated;
first optical means provided in said first optical path of said observing system for adjusting an objective plane observable from said slit-lamp microscope; and second optical means provided in said second optical path of said laser optical system for adjusting a focal point, said laser beam being controlled while adjusting said focal point along said second optical path of the laser optical system;

wherein said first optical means controls the movement of the objective plane observed by said observing system according to said predetermined characteristics of said contact lens and said second optical means adjusts the focal point to focus the laser beam on the objective plane;

wherein said second optical means is a lens movable along the second optical path of the laser optical system.

18. The apparatus according to claim 17, wherein said contact lens has an optical characteristics to allow an image of a fundus of the eye to be focused on a plane in front of the eye.

19. The apparatus according to claim 17, wherein said contact lens has an optical characteristics to prevent refracting power from the cornea of the eye to be treated and to allow an image of a fundus of the eye to be observed.

20. An apparatus for performing an ophthalmic operation on an eye by photocoagulation using a laser beam while allowing continuous observation of the eye to be treated, comprising:

a light source for producing the laser beam;

an observing system having a first optical path including a slit-lamp microscope;

a laser optical system having a second optical path;

means for transmitting said laser beam from said light source to said laser optical system;

means for introducing the laser beam from said second optical path of said laser optical system to said first optical path of said observing system;

first optical means provided in said first optical path of said observing system for adjusting an objective plane observable from said slit-lamp microscope;

first driving means for driving said first optical means;

second optical means provided in said second optical path of said laser optical system for adjusting a focal point, said laser beam being movably controlled while adjusting said focal point along said second optical path of the laser optical system;

second driving means for driving said second optical means;

a plurality of contact lenses each having predetermined optical characteristics;

switching means for selecting one of said plurality of contact lenses to be positioned in front of and contacting the eye to be treated, said switching means producing a signal; and control means for receiving said signal from said switching means and controlling said first and second driving means according to said signal.

* * * * *

UNITED STATES PATENT AND TRADEMARK OFFICE
CERTIFICATE OF CORRECTION

PATENT NO. : 5,226,903

DATED : July 13, 1993

INVENTOR(S) : Katsuyasu Mizuno

It is certified that error appears in the above-indentified patent and that said Letters Patent is hereby corrected as shown below:

Claim 9, column 11, line 30, change "characteristics" to --characteristic--.

Claim 14, column 12, line 13, change "slip-lamp" to --slit-lamp--.

Claim 17, column 12, line 57, change "slip-lamp" to --slit-lamp--.

UNITED STATES PATENT AND TRADEMARK OFFICE
CERTIFICATE OF CORRECTION

PATENT NO. : 5,226,903
DATED : July 13, 1993
INVENTOR(S) : Katsuyasu Mizuno

It is certified that error appears in the above-indentified patent and that said Letters Patent is hereby corrected as shown below:

Claim 18, column 13, line 18, change "characteristics" to --characteristic--.

Claim 19, column 13, line 22, change "characteristics" to --characteristic--.

Signed and Sealed this

Twenty-sixth Day of July, 1994

Attest:

BRUCE LEHMAN

Attesting Officer

Commissioner of Patents and Trademarks